United States Patent [19]

Hinnenkamp

[11] Patent Number: 5,064,865

[45] Date of Patent: Nov. 12, 1991

[54] CRYSTALLINE ALUMINOSILICATE COMPOSITIONS, THE PREPARATION THEREOF AND THEIR USE IN THE CONVERSION OF SYNTHESIS GAS TO LOW MOLECULAR WEIGHT HYDROCARBONS

[75] Inventor: James A. Hinnenkamp, Cincinnati, Ohio

[73] Assignee: Quantum Chemical Corporation, New York, N.Y.

[21] Appl. No.: 630,471

[22] Filed: Dec. 19, 1990

Related U.S. Application Data

[60] Division of Ser. No. 201,663, Jun. 2, 1988, Pat. No. 4,980,326, and a continuation-in-part of Ser. No. 117,453, Oct. 26, 1987, abandoned, which is a continuation of Ser. No. 750,119, Jul. 1, 1985, abandoned.

[51] Int. Cl.$^5$ ............................................. C07C 1/04
[52] U.S. Cl. ...................................... 518/713; 518/714
[58] Field of Search ................................ 518/717, 714

[56] References Cited

U.S. PATENT DOCUMENTS

| | | | |
|---|---|---|---|
| 3,140,249 | 7/1964 | Plank et al. | 208/120 |
| 3,140,251 | 7/1964 | Plank et al. | 208/120 |
| 3,140,253 | 7/1964 | Plank et al. | 208/120 |
| 3,702,886 | 11/1972 | Argauer et al. | 423/328 |
| 3,709,979 | 1/1973 | Chu | 423/328 |
| 3,832,449 | 8/1974 | Rosinski et al. | 423/328 |
| 3,884,835 | 5/1975 | Vaughan | 252/451 |
| 3,941,871 | 3/1976 | Dwyer et al. | 423/326 |
| 4,046,859 | 9/1977 | Plank et al. | 423/328 |
| 4,088,605 | 5/1978 | Rollmann | 252/455 |
| 4,298,695 | 11/1981 | Butter et al. | 518/720 |
| 4,418,155 | 11/1983 | Chang et al. | 518/719 |
| 4,468,474 | 8/1984 | Gupta et al. | 502/5 |
| 4,472,535 | 9/1984 | Chang et al. | 518/714 |

*Primary Examiner*—Howard T. Mars
*Attorney, Agent, or Firm*—Kenneth D. Tremain; Gerald A. Baracka

[57] ABSTRACT

Crystalline platinum or palladium aluminosilicates are prepared by incorporating platinum or palladium onto the aluminosilicate and mixing with a methanol synthesis catalyst. Conversion of synthesis gas to low molecular weight hydrocarbons, particularly $C_{2+3}$ hydrocarbons, with substantial yield and high selectivity employing these platinum or palladium aluminosilicate compositions as catalysts are also disclosed.

3 Claims, No Drawings

CRYSTALLINE ALUMINOSILICATE COMPOSITIONS, THE PREPARATION THEREOF AND THEIR USE IN THE CONVERSION OF SYNTHESIS GAS TO LOW MOLECULAR WEIGHT HYDROCARBONS

CROSS-REFERENCE TO RELATED APPLICATIONS

This is a divisional of copending application Ser. No. 201,663, filed on June 2, 1988, now U.S. Pat. No. 4,980,326, which is a continuation-in-part of application Ser. No. 117,453, filed Oct. 26, 1987, now abandoned, which is a continuation of application Ser. No. 750,119, filed July 1, 1985, now abandoned.

BACKGROUND OF THE INVENTION

1. Field of the Invention

The present invention relates to aluminosilicate compositions and the catalytic conversion of synthesis gas to low molecular weight hydrocarbons utilizing these compositions.

2. Discussion of the Prior Art

Zeolite materials, both natural and synthetic, are known to have catalytic capability for various types of reactions, especially hydrocarbon conversions. The well known crystalline aluminosilicate zeolites are commonly referred to as "molecular sieves" and are characterized by their highly ordered crystalline structure and uniformly dimensioned pores, and are distinguishable from each other on the basis of composition, crystal structure, adsorption properties and the like. The term "molecular sieves" is derived from the ability of the zeolite materials to selectively adsorb molecules on the basis of their size and form.

The processes for producing such crystalline synthetic zeolites are well known in the art. A family of crystalline aluminosilicate zeolites, designated ZSM-5, is disclosed in U.S. Pat. No. 3,702,886, said patent being incorporated herein by reference.

U.S. Pat. No. 3,941,871 relates to novel crystalline metal organosilicates which are essentially free of Group IIIA metals, i.e., aluminum and/or gallium. This patent is incorporated herein by reference. It is noted therein that the amount of alumina present in the known zeolites appears directly related to the acidity characteristics of the resultant product and that a low alumina content has been recognized as being advantageous in attaining a low degree of acidity which in many catalytic reactions is translated into low coke making properties and low aging rates. A typical procedure for making the organosilicates is to react a mixture containing a tetraaklylammonium compound, sodium hydroxide, and oxide of a metal other than a metal of Group IIIA, an oxide of silicon, and water until crystals of said metal organosilicates are formed. It is also noted in the patent that the family of crystalline metal organosilicates have a definite X-ray diffraction pattern which is similar to that of the ZSM-5 zeolites. Minor amounts of alumina are contemplated in the patent and are attributable primarily to the presence of aluminum impurities in the reactants and/or equipment employed.

U.S. Pat. No. 3,884,835 discloses crystalline silica compositions. The crystalline silica materials may also contain a metal promoter which may be selected from Group IIIA, Group VB or Group VIB elements. Boron is disclosed as one of the metal promoters.

U.S. Pat. No. 4,088,605 is directed to the synthesis of a zeolite, such as ZSM-5, which contains an outer shell free from aluminum. The patent states at column 10, the paragraph beginning at line 20, that to produce the outer aluminum-free shell, it is also essential that the reactive aluminum be removed from the reaction mixture. It is therefore necessary, as noted therein, to process the zeolite and to replace the crystallization medium with an aluminum-free mixture to obtain crystallization of $SiO_2$ on the surface of the zeolite which can be accomplished by a total replacement of the reaction mixture or by complexing from the original reaction mixture any remaining aluminum ions with reagents such as gluconic acid or ethylenediaminotetraacetic acid (EDTA).

Crystalline borosilicate compositions are disclosed in Germany Offenlegungschrift 2,746,790. This application relates specifically to borosilicates which are prepared using the usual procedures for making the aluminosilicate zeolites. It is noted therein that in instances where a deliberate effort is made to eliminate aluminum from the borosilicate crystal structure because of its adverse influence on particular conversion processes, the molar ratios of $SiO_2/Al_2O_3$ can easily exceed 2000–3000 and that this ratio is generally only limited by the availability of aluminum-free raw materials.

Germany Offenlegungschrift 2,848,849 relates to crystalline aluminosilicates of the ZSM-5 zeolite series. These particular zeolites have a silica to alumina mole ratio greater than 20 and are prepared from a reaction mixture containing a source of silica, alumina, a quaternary alkyl ammonium compound and a metal compound including such Group VIII metals as ruthenium, palladium and platinum. In Example 2, the crystalline aluminosilicate is prepared from a reaction mixture containing $RuCl_3$ and in Example 3, the reaction mixture contains $H_2PtCl_6.nH_2O$.

U.S. Patent No. 4,468,474 discloses hydrogen activated catalyst compositions comprising iron, silicon and carbon that selectively convert gaseous mixtures to $C_2$–$C_6$ alkenes. It is further noted that the catalysts maintained their activity and high selectivity over a long period and that regeneration of partially deactivated catalysts can be accomplished by treatment with hydrogen at elevated temperature.

U.S. Pat. No. 4,298,695 discloses the conversion of sythesis gas to a liquid hydrocarbon, e.g. naphtha. The process employs unpromoted catalysts which need promoters and high activity without aging is characteristic of these catalysts.

U.S. Pat. No. 4,481,155 discloses a process for the conversion of synthesis gas utilizing a catalyst which comprises a ZSM-5 type zeolite and a carbon oxide reducing component. This process yields a particular product, e.g. linear alpha-olefins, ($C_4$–$C_6$ olefins).

U.S. Pat. No. 4,732,535 discloses a process for the conversion of synthesis gas to an exclusive hydrocarbon product with selectivity to ethane. The catalysts comprise a crystalline zeolite component and a metal component. The zeolites employed are primarily synthetic zeolites such as ZSM-5, ZSM-11 and the like, that have a silica:alumina ratio of at least 12:1 and preferably 30:1. The metal component may be derived from one or more metals. Suitable metals or combinations of metals are those which may be employed for the synthesis of alcohols from synthesis gas. The metal components may be introduced into the zeolite by impregnation from liquid ammonia solutions. In Example 10, the effect of using different zeolites, e.g. erionite (a natural zeolite) is shown in the conversion of synthesis gas. Erionite shows significantly lower selectivity for ethane.

While the art has provided zeolitic catalysts having a wide variety of catalytic and adsorbtive properties, the need still exists for crystalline materials having different and/or enhanced catalytic properties. For example, an important use for a catalytic material is the conversion of synthesis gas to low molecular weight hydrocarbons. Further, many hydrocarbon conversion processes are performed employing zeolites, i.e. alkylation and isomerization. As is well-known in the art, it is important to maximize selectivity for a desired product. Accordingly it is one object of the present invention to provide novel crystalline aluminosilicate compositions.

Accordingly it is another object of this invention to provide aluminosilicate compositions having different and enhanced catalytic properties.

Another object of the invention herein is to provide a new method for the preparation of these novel crystalline aluminosilicate compositions.

A further object of this invention is to provide an improved method for the conversion of hydrocarbons and oxygenated compounds to selected end products.

A still further object of this invention is to provide an improved method for the conversion of synthesis gas to low molecular weight hydrocarbons utilizing aluminosilicate compositions.

The achievement of these and other objects will be apparent from the following description of the subject invention.

SUMMARY OF THE INVENTION

These and other objects are achieved by incorporating palladium or platinum onto the aluminosilicates and mixing the aluminosilicates with a methanol synthesis catalyst for use in converting synthesis gas to low molecular weight hydrocarbons. Briefly, this invention relates to novel platinum or palladium aluminosilicate compositions that can be physically mixed with a methanol synthesis catalyst, the preparation of these compositions and the use of these compositions to convert synthesis gas to low molecular weight hydrocarbons, preferably $C_{2+3}$ hydrocarbons. Consequently, when compositions prepared in accordance with the present invention are used in the conversation of synthesis gas to low molecular weight hydrocarbons, the compositions exhibit high catalytic activity in the conversion of synthesis gas to $C_2$-$C_4$ hydrocarbons, with high selectivity specifically for $C_{2+3}$ hydrocarbons. These properties are contrary to the results expected from this type of crystalline zeolite composition.

The compositions of this invention are prepared by a method which comprises:
  (a) contacting a crystalline aluminosilicate with a platinum or palladium salt solution to provide a platinum or palladium crystalline aluminosilicate containing about 0.2 to about 0.5% by weight of platinum or palladium, said crystalline aluminosilicate being ZSM-5 or chabazite;
  (b) calcining the platinum or palladium crystalline aluminosilicate in air at a temperature of about 300° C. to about 600° C. for at least 4 hours; and
  (c) heating the calcined platinum or palladium crystalline aluminosilicate in the presence of hydrogen from ambient temperature to an elevated temperature of about 300° C. to about 400° C. at a rate of temperature increase of about 0.5° to about 2.0° C. per minute,
  (d) maintaining said crystalline aluminosilicate at said temperature for about 0.75 to about 1.25 hours; and
  (e) cooling said crystalline aluminosilicate to ambient temperature in the presence of hydrogen.

In a further preparation, an additional step (f) is added to the above method:
  (f) mixing said aluminosilicate with a methanol synthesis catalyst in a weight ratio of methanol synthesis catalyst to aluminosilicate of about 0.3 to about 5.0.

In another embodiment, this invention relates to aluminosilicate compositions that are prepared by the method or methods described above.

Still another embodiment of this invention relates to a method for the conversion of synthesis gas comprising:
contacting synthesis gas which comprises hydrogen and carbon monoxide with a catalytically effective amount of the crystalline aluminosilicate compositions described above under conversion conditions effective to provide $C_{2+3}$ hydrocarbons at a carbon selectivity of at least about 80% and a carbon yield of at least about 20%.

DETAILED DESCRIPTION OF THE INVENTION

This invention relates to a method of preparing aluminosilicates and the catalytic conversion of synthesis gas utilizing these aluminosilicates to $C_{2-4}$ hydrocarbons, with high selectivity for $C_{2+3}$ hydrocarbons.

Zeolitic materials, both natural and synthetic, in naturally occurring and modified forms have been demonstrated as having catalytic capabilities for hydrocarbon conversion. Such zeolitic materials are ordered crystalline aluminosilicates having definite crystalline structure within which there are passages, pores, or cavities of definite ranges of sizes. Since the dimensions of these pores are such as to accept for adsorption molecules of certain dimensions while rejecting those of larger dimension, these materials have been referred to as "molecular sieves" and utilized in many ways taking advantage of these properties.

The aluminosilicates of this invention may be prepared by incorporating platinum or palladium onto various known zeolites. Platinum is the preferred species because of the improved catalyst stability it provides. The incorporation of either metal may be achieved by ion-exchange or impregnation.

Ion-exchange techniques known to those in the art may utilized. For example, typical ion-exchange techniques include contacting the aluminosilicates with a salt solution of the desired replacing cation or cations. Although a wide variety of salts can be employed, particular preference is given to chlorides, nitrates and sulfates.

Representative ion-exchange techniques are disclosed in a wide variety of patents including U.S. Pat. Nos. 3,140,249, 3,140,251 and 3,140,253, which are incorporated herein by reference.

Alternatively, platinum or palladium may be impregnated into the aluminosilicate by the addition of an ammonia solution or an aqueous solution of an appropriate platinum or palladium salt. The ammonia solvent which is used may be liquid ammonia or aqueous ammonia containing greater than 50 weight percent ammonia. Prior to impregnation with either solution, the aluminosilicate should, if necessary, be calcined at about 300° C.

to about 600° C. for at least 4 hours in air or an inert atmosphere to drive off any organic cations which remain after formation of the aluminosilicate and which would tend to block the pore structure of the aluminosilicate.

Addition of the ammonia solvent dissolves the platinum or palladium and the resulting solution is added to the aluminosilicate. After impregnation, the aluminosilicate is dried, generally under mild conditions, to drive off the solvent and fix the platinum or palladium on the aluminosilicate. Temperatures of up to about 200° C., preferably about 110° C. to about 130° C. are suitable for this purpose.

The percent by weight of platinum or palladium that is used to ion-exchange or impregnate the aluminosilicate significantly affects the catalytic activity, stability and selectivity for $C_{2+3}$ hydrocarbons in the conversion of synthesis gas. The percent by wt. of platinum or palladium present in the aluminosilicate should be about 0.1% wt. to about 10% wt., with about 0.2% wt. to about 5.0% wt being preferred. The aluminosilicate must have at least 0.1% wt. of platinum or palladium present in the composition in order to obtain good selectivity and stability for the conversion of synthesis gas to $C_{2+3}$ hydrocarbons.

Various metals may be ion-exchanged or alternatively impregnated onto the aluminosilicates in accordance with this invention. Group VIII metals are intended to be included in the scope of this invention, with platinum and palladium being preferred and platinum being specifically preferred. The description herein will utilize platinum for illustrative purposes, it being understood that palladium may be employed instead.

The aluminosilicates that are prepared in accordance with the present invention and used in the conversion of synthesis gas are know in the art. The term aluminosilicate is meant to include synthetically produced and naturally occurring aluminosilicates. The aluminosilicates intended to be included in the scope of this invention include ZSM-5, ZSM-11, ZSM-34, ZSM-38, chabazite, erionite, and of which ZSM-5, and chabazite are preferred.

ZSM-5 is fully disclosed in U.S. Pat. No. 3,702,886, the disclosure of which is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-38 is described in U.S. Pat. No. 4,046,859, the entire contents of which are incorporated herein by reference.

Platinum or palladium exchanging the aluminosilicates in accordance with the present invention affects the selectivity and stability of the aluminosilicates in the conversion of synthesis gas to low molecular weight $C_{2+3}$ hydrocarbons.

In an optional embodiment of this invention, the physical mixing of commercially available methanol synthesis catalysts, such as for example, a copper oxide-zinc oxide or a chromium oxide-zinc oxide catalyst with the platinum aluminosilicate increases the catalytic conversion of synthesis gas to $C_{2+3}$ hydrocarbons. The copper-zinc catalyst available from United Catalyst Inc. under the designation "C18HC", has a high activity and its composition is a 1:1 ratio of ZnO to CuO plus 10% alumina. The chromium-zinc catalyst, available from Harshaw Chemical Co. under the designation "Zn-0312 T," is composed of 74% ZnO, 21% chromium oxide and 600 parts per million of aluminum. High hydrocarbon yields result when the methanol synthesis catalyst is added in a weight ratio of about 0.1 to 10 preferably about 0.3 to 5, in relation to the amount of platinum aluminosilicate.

The methanol synthesis catalyst may be physically mixed with the platinum aluminosilicate composition by any known method, such as for example, blending, ultrasonic mixing and the like.

The aluminosilicates of this invention are platinum exchanged and heat treated in air at 540° C. for 4 hours and then cooled to ambient temperature. The aluminosilicates are then subjected to a hydrogen treatment during which the treating temperature is increased from ambient conditions to about 200° C. to about 500° C., preferably about 300° C. to about 400° C. The rate of temperature increase must be controlled. A temperature increase of about 0.1° C. to about 5.0° C. per minute with a temperature increase of about 0.5° C. to 2.0° C. per minute being preferred. After reaching the desired temperature, the composition is maintained at this temperature for about 0.5 to about 4 hours, preferably about 0.75 hour to about 1.25 hour. The composition is then cooled to ambient temperature in the pressence of an inert gas or hydrogen. The treatment of the composition with hydrogen during the heat treatment and cooling steps increases the $C_{2+3}$ hydrocarbon selectivity and activity when the composition is employed in the conversion of synthesis gas to low molecular weight hydrocarbons.

The present invention provides physical mixtures of crystalline aluminosilicates and methanol synthesis catalysts which exhibit superior catalytic activity for the highly selective conversion of synthesis gas (carbon monoxide and hydrogen) to low molecular weight hydrocarbons ($C_{2+3}$ hydrocarbons). Moreover, these compositions of the present invention maintain their catalytic activity and high selectivity over relatively long periods of time. An advantage of this process is that any water formed reacts with the CO in the water gas shift reaction to provide additional quantities of hydrogen. For this reason there is little need to employ a water gas shifted synthesis gas as the feed in the process of this invention.

Synthesis gas is provided commercially by such well known processes as the steam reforming of naphtha or natural gas or the partial oxidation of carbonaceous materials, such as coal or heavy petroleum distillates. The reations involved are:

Steam Reforming:

$$C_nH_{(2n+2)} + nH_2O \longrightarrow nCO + (2n + 1)H_2$$

Partial Oxidation:

$$4C + 2H_2O + O_2 \longrightarrow 2H_2 + 4CO$$

or $$C_nH_{(2n+2)} + (n/2)O_2 \longrightarrow nCO + (n + 1)H_2$$

The process for conversion of mixtures of gaseous carbon monoxide and hydrogen in the presence of an effective amount of the compositions of the present invention is conveniently conducted at a temperature in the range of about 250° to about 500° C., normally 325°–500° C., a pressure in the range of about 0 psig (101 kPa) to about 1500 psig (10,442 kPa), preferably 50 psig (446 kPa)-1000 psig (6995 kPa), in a batch or flow reactor system. The volume ratio of carbon monoxide to hydrogen is conveniently in the range of 0.5:1 to about 6:1, normally about 1:1.

The process of the present invention is conducted for a time sufficient to form a product mixture containing methane, $C_2$–$C_6$ hydrocarbons, carbon dioxide, water and less than 5.0% alcohols and ethers. The product mixture may be entrapped in a suitable trapping means such as a condenser and thereafter separated by standard techniques, e.g. distillation. For example, when utilizing the subject process in a batch-wise fashion, contact times of about 0.1 to about 3.0, preferably about 0.5 to about 2 minutes are found to be effective. When reacting the subject process continuously space velocities of about 0.1 to about 20, preferably about 0.5 to about 10 weight hourly space velocity (WHSV) should be utilized.

The activity of the compositions of the present invention is achieved at temperatures of about 325°–450° C. Furthermore, the composition deactivates faster at temperatures of about 450° C. to about 500° C. The activity of the composition is decreased at temperatures of about 300° C. to about 325° C. Temperatures in the range of about 325° C. to about 450° C. were preferred for maximizing catalytic activity, service lifetime and selectivity to $C_{2+3}$ hydrocarbons.

The process of the present invention can by operated in batch or continuous mode. A continuous flow reactor minimizes secondary reactions of initially formed products and extends the service lifetime of the composition.

Synthetic crystalline aluminosilicate compositions of this invention, when evaluated for catalytic properties without having been calcined, are inactive, possibly because the intracrystalline free space is occupied by organic cations from the forming solution. They may, however, be activated by heat treatment using known techniques such as heating in an inert atmosphere or air at 200°–900° C., for 1 to 60 hours. This may be followed by ion-exchange with ammonium salts and further heat treatment at 200°–900° C. if desired. Typical ion-exchange techniques as described above may be employed to platinum or palladium exchange the aluminosilicate.

Regardless of the cations replacing the sodium in the synthesized form of the composition, the spatial arrangement of the atoms which form the basic crystal lattices in any given composition of this invention remain essentially unchanged by the described replacement of sodium or other alkali metal as determined by taking an X-ray powder diffraction pattern of the ion-exchanged material.

The aluminosilicate compositions prepared by the instant invention are formed in a wide variety of particular sizes. Generally speaking, the particles can be in the form of a powder, a granule, or a molded product, such as extrudate having a particle size sufficient to pass through a 2 mesh (Tyler) screen and be retained on a 100 mesh (Tyler) screen. In cases where the composition is molded, such by extrusion, the composition can be extruded before drying or dried or partially dried and then extruded.

In the case of the mixtures of methanol synthesis catalyst and platinum aluminosilicate the mixing can occur before or after the extrusion process. It should be remembered that where the methanol synthesis catalyst is present before the heat treatment, the treatment conditions should be chosen not to adversely affect the methanol synthesis catalyst.

In the case of many catalysts, it is desired to incorporate the aluminosilicate composition of this invention with another material resistant to the temperatures and other conditions employed in organic conversion processes. Such materials include active and inactive materials and synthetic or naturally occurring crystalline compositions as well as inorganic materials such as clays, silica and or metal oxides. The latter may be either naturally occurring or in the form of gelatinous precipitates or gels including mixtures of silica and metal oxides. Use of these materials in conjunction with the present composition tends to improve the conversion and/or selectivity of the catalyst in certain organic conversion processes. Inactive materials suitably serve as dilutents to control the amount of conversion in a given process so that products can be obtained economically and in an orderly manner without employing other means for controlling the rate of reaction. Normally, zeolite materials have been incorporated into naturally occurring clays, e.g., bentonite and kaolin, to improve the crush strength of the composition under commercial operating conditions. These materials, e.g., clays, oxides, etc. function as binders for the composition. It is desirable to provide a composition having good crush strength, because in a chemical process the composition is often subjected to handling or use which tends to break the composition down into powder-like materials which cause problems in processing. These clay binders have been employed for the purpose of improving the crush strength of the composition.

In addition to the foregoing materials, the aluminosilicate can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel.

The following examples are presented as specific embodiments of the present invention and show some of the unique characteristics of the claimed crystalline compositions and are not to be considered as constituting a limitation on the present invention.

EXAMPLE 1

A. Ion Exchange

1. $NH_4^+$ or $H^+$ Chabazite 25 grams of aluminosilicate (Linde AW500 Chabazite) were added to a solution of 15 grams $NH_4Cl$ dissolved in 400 ml deionized water and refluxed for 16 hours. The solution was then decanted and additional solution containing 15 grams $NH_4Cl$ dissolved in 400 ml deionized water were added. After 4 hours of reflux the solid was washed by repetitive decantation and isolated by filtration. Drying at 110° C. overnight yielded $NH_4^+$ - chabazite. If the $H^+$ form was desired, the $NH_4^+$ form was calcined at 540° C. in air or inert gas for 4 hours.

2. Pt-Chabazite

A 25 gram sample of $NH_4^+$-Chabazite aluminosilicate was added to a solution containing 0.53 gram Pt $(NH_3)_4Cl_2$ (56.15% Pt) dissolved in 400 ml deionized water. After being stirred at reflux for 16 hours, the solution was decanted and another charge of $Pt(NH_3)_4Cl_2$ and water was added, followed by stirring at reflux for 4 hours. After cooling the solid was washed by repeated decantation with water, collected by filtration, and dried overnight at 110° C.

B. Catalyst Pretreatment

Before charging Pt-aluminosilicate to the reactor, the preferred pretreatment was to calcine 25 grams of platinum- aluminosilicate in air at 540° C. for 4 hours and then cool to ambient temperature. The calcined solid was treated with 5% hydrogen in nitrogen at a temperature program of 1° C./minute to 350° C. and held for 1 hour. The catalyst was then cooled to ambient temperature in 5% hydrogen.

C. Physical Mixture

The Pt-aluminosilicate was physically mixed with a methanol synthesis catalyst (Harshaw's Zn-0312 T). Typically, 3 ml (4.1 grams) of the Cr-Zn methanol synthesis catalyst were added to the 6 ml (3.2 grams) of platinum-chabazite. The mixture was blended and changed to the reactor.

EXAMPLE 2

A physical mixture of a palladium - ZSM-5 and a methanol synthesis catalyst was prepared in accordance with the procedure of Example 1 except that palladium was substituted for platinum and ZSM-5 was substituted for chabazite.

EXAMPLE 3

This example compares the catalytic activities of platinum chabazite (platinum exchanged ammonium form of Linde AW500), a Cr-Zn methanol synthesis catalyst (Harshaw's Zn-0312 T), Cr-Zn followed by Pt-AW500, and a physical mixture of these two materials. The platinum compositions were prepared in accordance with Example 1 and all runs were conducted at 735 psig (5169 kPa) in a 310 stainless steel tubular reactor.

TABLE III

| | SYNGAS REACTIONS (1) | | | |
|---|---|---|---|---|
| Catalyst (2) | Cr—Zn | Pt-AW500 | Cr—Zn (3) Pt-AW500 | Cr—Zn Pt-AW500 (physical mixture) |
| $C_{2+3}$ Yield, % (4) | 2 | 4 | 8 | 34 |
| $C_{2+3}$ Sel., % (4) | 31 | 79 | 75 | 86 |
| HC Yield, % (4) | 5 | 5 | 11 | 40 |
| HC Sel., % (4) | | | | |
| $C_1$ | 69 | 21 | 22 | 10 |
| $C_2$ | 27 | 46 | 44 | 53 |
| $C_3$ | 4 | 33 | 31 | 33 |
| $C_4$ | 0 | 0 | 4 | 5 |
| $C_{5+}$ | 0 | 0 | 0 | 0 |
| Ar | 0 | 0 | 0 | 0 |
| $CO_2$ Yield, % (4) | 5 | 4 | 9 | 36 |
| CO Conv., % (4) | 11 | 9 | 20 | 76 |

(1) 400° C., $H_2$/CO = 1, 735 psig (5169 kPa), 9.86 l/h STP.
(2) 3 ml Cr—Zn, Harshaw Zn-0312 T and/or 6 ml Pt-AW500, Pt exchanged $NH_4^+$ AW500, prepared from Linde AW500.
(3) Cr—Zn followed by ¼" glass wool followed by Pt-AW500.
(4) Based on carbon.

The data show that the physically mixed Cr-Zn/PtAW500 composition of the present invention had the highest carbon monoxide conversion and the highest $C_{2+3}$ yield and selectivity for the conversion of synthesis gas. Both the Cr-Zn and the Pt-AW500 catalysts showed low carbon monoxide conversion, with the layered Cr-Zn/Pt-AW500 composition demonstrating a CO conversion equal to the sum of the conversion of the Cr-Zn and Pt-AW500 catalysts.

EXAMPLE 4

This example shows the effect of incorporating platinum onto chabazite (AW500) which is physically mixed with a Cr-Zn methanol synthesis catalyst for the conversion of synthesis gas. Both compositions were prepared in accordance with Example 1 and only differed in Pt content. All runs were conducted at 735 psig (5169 kPa) in a 310 stainless steel tubular reactor at an actual hourly space velocity of 60.

TABLE IV

| | SYNGAS REACTIONS (1) EFFECT OF PLATINUM ON AW500 MIXED WITH CHROMIUM—ZINC (3) | | | | | | | | | | | | |
|---|---|---|---|---|---|---|---|---|---|---|---|---|---|
| Pt, Wt. % | 0 | | | | | 2.0 | | | | | | | |
| Time on Stream, hrs. | 4 | 24 | 29 | 98 | 101 | 2 | 22 | 26 | 46 | 51 | 70 | 74 | 92 |
| $C_{2+3}$ Yield, % (2) | 24 | 14 | 13 | 10 | 10 | 35 | 35 | 34 | 34 | 34 | 33 | 34 | 32 |
| $C_{2+3}$ Sel., % (2) | 75 | 69 | 70 | 73 | 71 | 84 | 85 | 85 | 85 | 86 | 85 | 86 | 85 |
| HC Yield, % (2) | 32 | 20 | 19 | 14 | 14 | 42 | 41 | 40 | 40 | 39 | 39 | 39 | 38 |
| HC Sel., % (2) | | | | | | | | | | | | | |
| $C_1$ | 13 | 19 | 20 | 23 | 26 | 12 | 10 | 10 | 10 | 9 | 9 | 9 | 9 |
| $C_2$ | 25 | 38 | 40 | 44 | 43 | 50 | 47 | 48 | 46 | 46 | 45 | 47 | 46 |
| $C_3$ | 50 | 31 | 30 | 29 | 28 | 34 | 38 | 37 | 39 | 40 | 40 | 39 | 39 |
| $C_4$ | 7 | 8 | 7 | 3 | 3 | 4 | 5 | 5 | 5 | 5 | 5 | 5 | 6 |
| $C_{5+}$ & Ar | 5 | 5 | 4 | 0 | 0 | 0 | 0 | 0 | 0 | 0 | 0 | 0 | 0 |
| $CO_2$ Yield, % (2) | 31 | 19 | 18 | 14 | 14 | 35 | 34 | 33 | 32 | 33 | 32 | 33 | 33 |

TABLE IV-continued

SYNGAS REACTIONS (1)
EFFECT OF PLATINUM ON AW500
MIXED WITH CHROMIUM—ZINC (3)

| Pt, Wt. % | 0 | | | | | | 2.0 | | | | | | |
|---|---|---|---|---|---|---|---|---|---|---|---|---|---|
| CO Conv., % | 63 | 39 | 37 | 28 | 28 | 75 | 75 | 73 | 72 | 72 | 71 | 72 | 71 |

(1) 400° C., $H_2/CO = 1$, 735 psig (5169 kPa), Actual Hourly Space Velocity = 60.
(2) Based on carbon.
(3) Weight ratio: Cr—Zn/Pt-AW500 = 1.3

The data show that platinum-exchanged AW5000 which was mixed with Cr-Zn provided improved catalytic stability, higher $C_{2+3}$ selectivity, and higher hydrocarbon yield for synthesis gas conversion than the $H^+$-AW5000 (prior art type) composition.

EXAMPLE 5

This example compares the effect of the platinum content on the catalytic properties of physically mixed Cr-Zn/AW500 compositions for the conversion of synthesis gas. All of the compositions were prepared in accordance with Example 1, except that platinum was impregnated onto the $NH_4^+$ form of the compositions with aqueous $Pt(NH_3)_4Cl_2$. All runs were conducted at 735 psig (5169 kPa) in a 310 stainless steel tubular reactor at an actual hourly space velocity of 50.

TABLE V A

SYNGAS REACTIONS
THE EFFECT OF PLATINUM CONTENT
IN PT-AW500 MIXED WITH CHROMIUM—ZINC (1) (3)

| Pt, Wt. % (2) | 0.2 | | | | | | 0.5 | | | | | |
|---|---|---|---|---|---|---|---|---|---|---|---|---|
| Time, hrs. | 3 | 26 | 45 | 50 | 70 | 74 | 3 | 20 | 25 | 45 | 49 | 68 |
| $C_{2+3}$ Yield, % (4) | 30 | 28 | 23 | 23 | 21 | 20 | 32 | 29 | 29 | 28 | 28 | 27 |
| $C_{2+3}$ Sel., % (4) | 87 | 85 | 83 | 84 | 83 | 82 | 88 | 87 | 86 | 86 | 85 | 85 |
| HC Yield, % (4) | 35 | 33 | 28 | 27 | 25 | 24 | 36 | 33 | 34 | 33 | 33 | 32 |
| HC Sel., % (4) | | | | | | | | | | | | |
| $C_1$ | 6 | 7 | 10 | 10 | 11 | 12 | 6 | 7 | 8 | 8 | 8 | 8 |
| $C_2$ | 31 | 27 | 35 | 36 | 38 | 38 | 36 | 36 | 36 | 36 | 36 | 36 |
| $C_3$ | 56 | 58 | 48 | 48 | 45 | 44 | 52 | 51 | 50 | 50 | 49 | 49 |
| $C_4$ | 7 | 7 | 6 | 6 | 5 | 5 | 6 | 6 | 6 | 6 | 6 | 6 |
| $C_{5+}$ | 0 | 0 | 0 | 0 | 0 | 0 | 0 | 0 | 0 | 0 | 0 | 0 |
| Ar | 0 | 0 | 0 | 0 | 0 | 0 | 0 | 0 | 0 | 0 | 0 | 0 |
| $CO_2$ Yield, % (4) | 31 | 30 | 26 | 25 | 23 | 24 | 30 | 31 | 28 | 27 | 27 | 26 |
| CO Conv., % | 66 | 63 | 54 | 52 | 48 | 48 | 66 | 64 | 62 | 60 | 60 | 58 |

(1) 400° C., $H_2/CO = 1$, 735 psig (5169 kPa), Actual Hourly Space Velocity = 50.
(2) Nominal Values, Pt impregnated $NH_4^+$ - AW500.
(3) All catalysts mixed with Harshaw Cr—Zn weight ratio: Cr—Zn/Pt-AW500 = 1.3.
(4) Based on carbon.

TABLE V B

SYNGAS REACTIONS
THE EFFECT OF PLATINUM CONTENT
IN PT-AW500 MIXED WITH CHROMIUM—ZINC (1) (3)

| Pt, Wt. % (2) | 1.0 | | | | | | 2.0 | | | | | |
|---|---|---|---|---|---|---|---|---|---|---|---|---|
| Time, hrs. | 3 | 22 | 26 | 45 | 50 | 68 | 3 | 22 | 26 | 45 | 50 | 68 |
| $C_{2+3}$ Yield, % (4) | 26 | 24 | 24 | 23 | 23 | 22 | 31 | 29 | 29 | 28 | 27 | 26 |
| $C_{2+3}$ Sel., % (4) | 88 | 86 | 86 | 86 | 85 | 85 | 89 | 88 | 88 | 87 | 88 | 88 |
| HC Yield, % (4) | 30 | 28 | 28 | 27 | 27 | 26 | 35 | 33 | 33 | 32 | 31 | 30 |
| HC Sel., % (4) | | | | | | | | | | | | |
| $C_1$ | 6 | 7 | 8 | 8 | 8 | 8 | 6 | 6 | 6 | 7 | 6 | 7 |
| $C_2$ | 39 | 37 | 38 | 37 | 36 | 36 | 47 | 45 | 46 | 45 | 46 | 46 |
| $C_3$ | 49 | 49 | 48 | 49 | 49 | 49 | 42 | 43 | 42 | 42 | 42 | 42 |
| $C_4$ | 6 | 7 | 6 | 7 | 7 | 6 | 5 | 5 | 5 | 6 | 5 | 6 |
| $C_{5+}$ | 0 | 0 | 0 | 0 | 0 | 0 | 0 | 0 | 0 | 0 | 0 | 0 |
| Ar | 0 | 0 | 0 | 0 | 0 | 0 | 0 | 0 | 0 | 0 | 0 | 0 |
| $CO_2$ Yield, % (4) | 27 | 24 | 24 | 23 | 24 | 23 | 30 | 28 | 28 | 27 | 27 | 26 |
| CO Conv., % | 57 | 52 | 52 | 50 | 51 | 49 | 65 | 61 | 61 | 59 | 58 | 56 |

(1) 400° C., $H_2/CO = 1$, 735 psig (5169 kPa), Actual Hourly Space Velocity = 50.
(2) Nominal Values, Pt impregnated $NH_4^+$ - AW500.
(3) All catalysts mixed with Harshaw Cr—Zn weight ratio: Cr—Zn/Pt-AW500 = 1.3.
(4) Based on carbon.

TABLE V C

SYNGAS REACTION
THE EFFECT OF PLATINUM CONTENT
ON Pt-AW500 MIXED WITH CHROMIUM—ZINC (1) (3)

| Pt, Wt. % (2) | 3.0 | | | | | | 3.0 | | | | | |
|---|---|---|---|---|---|---|---|---|---|---|---|---|
| Time, hrs. | 3 | 20 | 25 | 45 | 49 | 68 | 4 | 32 | 27 | 46 | 51 | 69 |
| $C_{2+3}$ Yield, % (4) | 26 | 23 | 22 | 20 | 20 | 18 | 30 | 28 | 27 | 26 | 26 | 26 |
| $C_{2+3}$ Sel., % (4) | 87 | 87 | 85 | 84 | 85 | 83 | 88 | 88 | 86 | 87 | 87 | 88 |
| HC Yield, % (4) | 30 | 26 | 26 | 24 | 24 | 22 | 34 | 32 | 31 | 30 | 30 | 29 |

TABLE V C-continued

SYNGAS REACTION
THE EFFECT OF PLATINUM CONTENT
ON Pt-AW500 MIXED WITH CHROMIUM—ZINC (1) (3)

| Pt, Wt. % (2) | 3.0 | | | | | | 3.0 | | | | | |
|---|---|---|---|---|---|---|---|---|---|---|---|---|
| HC Sel., % (4) | | | | | | | | | | | | |
| $C_1$ | 7 | 8 | 8 | 10 | 10 | 10 | 7 | 7 | 7 | 8 | 8 | 7 |
| $C_2$ | 39 | 41 | 41 | 41 | 42 | 42 | 47 | 45 | 44 | 44 | 45 | 45 |
| $C_3$ | 48 | 46 | 44 | 43 | 43 | 41 | 41 | 43 | 42 | 43 | 42 | 43 |
| $C_4$ | 6 | 6 | 6 | 6 | 6 | 6 | 5 | 6 | 6 | 6 | 6 | 6 |
| $C_{5+}$ | 0 | 0 | 0 | 0 | 0 | 0 | 0 | 0 | 0 | 0 | 0 | 0 |
| Ar | 0 | 0 | 0 | 0 | 0 | 0 | 0 | 0 | 0 | 0 | 0 | 0 |
| $CO_2$ Yield, % (4) | 24 | 22 | 21 | 20 | 20 | 19 | 29 | 27 | 26 | 25 | 25 | 24 |
| CO Conv., % | 54 | 48 | 47 | 44 | 44 | 44 | 63 | 59 | 57 | 55 | 55 | 53 |

(1) 400° C., $H_2/CO$ = 1, 735 psig (5169 kPa), Actual Hourly Space Velocity = 50.
(2) Nominal Values, Pt impregnated $NH_4^+$ - AW500.
(3) All catalysts mixed with Harshaw Cr—Zn weight ratio: Cr—Zn/Pt-AW500 = 1.3.
(4) Based on carbon.

All of the compositions showed high $C_{2+3}$ selectivity for the conversion of synthesis gas. Further, all compositions had higher $C_{2+3}$ selectivity and better stability than platinum free compositions (See Table IV).

EXAMPLE 6

This example compares the effect of different weight ratios of chromium-zinc and platinum-AW500 on the catalytic properties of compositions of the present invention for the conversion of synthesis gas. All catalysts contained equivalent amounts of Pt-AW500 and the syngas feed rate was constant. However total catalyst volume varied with the amount of methanol catalyst added. All of the compositions were prepared in accordance with Example 1 and all runs were conducted at 735 psig (5160 kPa) in a 310 stainless steel tubular reactor.

TABLE VI A

SYNGAS REACTIONS
THE EFFECT OF Zn—Cr/Pt AW500 RATIO (1)

| Weight Ratio Zn—Cr/Pt-AW500 | 0.3 | | | | 0.7 | | |
|---|---|---|---|---|---|---|---|
| Time, hrs | 3 | 21 | 26 | 44 | 3 | 25 | 43 |
| $C_{2+3}$ Yield, % (2) | 20 | 19 | 19 | 19 | 27 | 26 | 25 |
| $C_{2+3}$ Sel., % (2) | 85 | 86 | 84 | 88 | 87 | 87 | 88 |
| HC Yield % | 23 | 22 | 23 | 22 | 31 | 30 | 28 |
| HC Sel., % (2) | | | | | | | |
| $C_1$ | 10 | 9 | 12 | 8 | 8 | 8 | 6 |
| $C_2$ | 47 | 45 | 44 | 46 | 47 | 46 | 45 |
| $C_3$ | 38 | 41 | 40 | 42 | 40 | 41 | 43 |
| $C_4$ | 4 | 4 | 4 | 4 | 5 | 5 | 4 |
| $C_{5+}$ & Ar | 0 | 0 | 0 | 0 | 0 | 0 | 0 |
| $CO_2$ Yield, % (2) | 19 | 18 | 18 | 18 | 26 | 24 | 24 |
| CO Conversion, % | 42 | 40 | 41 | 40 | 57 | 54 | 52 |

(1) 400° C., $H_2/CO$ = 1, 735 psig (5169 kPa), Actual Space Velocity = 65.
(2) Based on carbon.

TABLE VI B

SYNGAS REACTIONS
THE EFFECT OF Cr—Zn/Pt-AW500 RATIO (1)

| Weight Ratio Cr—Zn/Pt-AW500 | 1.3 | | | | | 1.9 | | | |
|---|---|---|---|---|---|---|---|---|---|
| Time, hrs | 3 | 22 | 26 | 46 | 50 | 3 | 21 | 25 | 43 |
| $C_{2+3}$ Yield, % (2) | 34 | 31 | 31 | 31 | 30 | 37 | 35 | 34 | 34 |
| $C_{2+3}$ Sel., % (2) | 86 | 87 | 87 | 88 | 87 | 88 | 86 | 87 | 86 |
| HC Yield, % (2) | 39 | 36 | 36 | 35 | 35 | 42 | 41 | 39 | 39 |
| HC Sel., % (2) | | | | | | | | | |
| $C_1$ | 9 | 8 | 7 | 7 | 7 | 8 | 9 | 7 | 8 |
| $C_2$ | 49 | 46 | 46 | 45 | 43 | 49 | 46 | 46 | 43 |
| $C_3$ | 37 | 41 | 41 | 43 | 44 | 39 | 40 | 41 | 43 |
| $C_4$ | 5 | 5 | 5 | 5 | 5 | 5 | 5 | 6 | 6 |
| $C_{5+}$ & Ar | 0 | 0 | 0 | 0 | 0 | 0 | 0 | 0 | 0 |
| $CO_2$ Yield, % (2) | 32 | 31 | 30 | 29 | 29 | 35 | 33 | 32 | 0 |

TABLE VI B-continued

SYNGAS REACTIONS
THE EFFECT OF Cr—Zn/Pt-AW500 RATIO (1)

| Weight Ratio Cr—Zn/Pt-AW500 | 1.3 | | | | | 1.9 | | | |
|---|---|---|---|---|---|---|---|---|---|
| CO Conversion, % | 71 | 67 | 66 | 64 | 64 | 77 | 74 | 71 | 69 |

(1) 400° C., $H_2/CO$ = 1, 735 psig, Actual Hourly Space Velocity = 40-50.
(2) Based on carbon.

TABLE VI C

SYNGAS REACTIONS
THE EFFECT OF Cr—Zn/Pt-AW500 RATIO (1)

| Weight Ratio Cr—Zn/Pt-AW500 | 2.6 | | | | |
|---|---|---|---|---|---|
| Time, Hrs. | 3 | 21 | 26 | 44 | 49 |
| $C_{2+3}$ Yield, % (2) | 41 | 40 | 39 | 38 | 38 |
| $C_{2+3}$ Sel., % (2) | 88 | 89 | 88 | 88 | 88 |
| HC Yield, % (2) | 47 | 45 | 44 | 43 | 43 |
| HC Sel., % (2) | | | | | |
| $C_1$ | 8 | 6 | 7 | 7 | 7 |
| $C_2$ | 51 | 48 | 47 | 47 | 47 |
| $C_3$ | 37 | 41 | 41 | 41 | 41 |
| $C_4$ | 4 | 4 | 5 | 5 | 5 |
| $C_{5+}$ & Ar | 0 | 0 | 0 | 0 | 0 |
| $CO_2$ Yield, % (2) | 38 | 37 | 38 | 37 | 37 |
| CO Conversion, % | 85 | 82 | 82 | 80 | 80 |

(1) 400° C., $H_2/CO$ = 1, 735 psig (5169 kPa), Actual Hourly space Velocity = 50.
(2) Based on carbon.

The data show that the weight ratio of Cr-Zn and Pt-AW500 had little effect on the $C_{2+3}$ selectivity for the conversion of synthesis gas. However, $C_{2+3}$ hydrocarbon yield increased as the amount of methanol catalyst (Cr-Zn) was increased. (See Table VI A—compositions having a Zn-Cr/Pt-AW500 ratio of 0.3 versus Table VI C—compositions having a Zn-Cr/Pt-AW500 of 2.6)

EXAMPLE 7

This example compares the effect of various methanol catalysts on the catalytic properties of the compositions of the present invention for the conversion of synthesis gas. All of the compositions were prepared in accordance with Example 1 and all runs were conducted at 735 psig (5169 kPa) in a 310 stainless steel tubular reactor at an actual hourly space velocity of 80.

TABLE VII

SYNGAS REACTIONS
VARIOUS METHANOL CATALYSTS
MIXED WITH Pt-AW500

| Catalyst | $C_{2+3}$ Yield, % | $C_{2+3}$ Sel., % |
|---|---|---|
| Cu—Zn (UCI C18HC) | 33 | 82 |
| Cu—Cr | 20 | 69 |
| Control (Pt-AW500 alone) | 4 | 79 |

400° C., $H_2/CO$ = 1, 735 psig (5169 kPa), Actual Hourly Space Velocity 80.

The data show methanol synthesis catalysts other than Cr-Zn enhance the catalytic properties of Pt-chabazite.

EXAMPLE 8

This example compares the effect of reaction temperatures on the catalytic properties and $C_{2+3}$ selectivity of a physically mixed composition of the present invention for the conversion of synthesis gas. The composition was prepared in accordance with Example 1, except that $NH_4^+$-AW500 zeolite was impregnated with aqueous Pt $(NH_3)_4Cl_2$. All runs were conducted at 735 psig (5169 kPa) in a 310 stainless steel tubular reactor at an actual hourly space velocity of 50.

TABLE VIII

EFFECT OF REACTION TEMPERATURE
ON Cr—Zn/Pt-AW500 FOR SYNGAS CONVERSION (1) (3)

| Temp, °C. | 350 | 400 | 450 |
|---|---|---|---|
| $C_{2+3}$ Yield, % (2) | 16 | 26 | 26 |
| $C_{2+3}$ Sel., % (2) | 80 | 88 | 88 |
| CO Conv., % (2) | 41 | 52 | 53 |
| HC Yield, % (2) | 20 | 29 | 29 |
| HC Sel., % (2) | | | |
| $C_1$ | 11 | 5 | 8 |
| $C_2$ | 30 | 37 | 46 |
| $C_3$ | 50 | 51 | 42 |

(1) $H_2/CO$ = 1, 735 psig (5169 kPa), Actual Hourly Space Velocity = 50.
(2) Based on carbon.
(3) Weight ratio: Cr—Zn/Pt-AW500 = 1.3

The data show that a Cr-Zn physically mixed Pt-AW500 composition had a higher $C_{2+3}$ selectivity at reaction temperatures above 350° C.

EXAMPLE 9

This example compares the effect of the $H_2/CO$ molar ratio on the catalytic properties of a composition of the present invention for the conversion of synthesis gas. The composition was prepared in accordance with Example 1 and all runs were conducted at 735 psig (5169 kPa) in a 310 stainless steel tubular reactor at an actual hourly space velocity of 50.

TABLE IX

SYNGAS REACTIONS
THE EFFECT OF HYDROGEN—CARBON MONOXIDE
RATIO ON Cr—Zn/Pt AW500 MIXTURES (1) (3)

| $H_2/CO$, molar | 0.5 | | | | 1.0 | | | | 2.0 | | | |
|---|---|---|---|---|---|---|---|---|---|---|---|---|
| Time, hrs. | 4 | 23 | 27 | 46 | 3 | 22 | 26 | 46 | 50 | 3 | 22 | 26 |
| $C_{2+3}$ Yield, % (2) | 23 | 18 | 17 | 14 | 34 | 31 | 31 | 31 | 30 | 40 | 37 | 37 |
| $C_{2+3}$ Sel., % (2) | 89 | 87 | 84 | 84 | 86 | 87 | 87 | 89 | 87 | 82 | 85 | 85 |
| HC Yield, % (2) | 26 | 21 | 20 | 17 | 39 | 36 | 36 | 35 | 35 | 49 | 44 | 43 |
| HC Sel., % (2) | | | | | | | | | | | | |
| $C_1$ | 8 | 9 | 11 | 12 | 9 | 8 | 7 | 7 | 7 | 12 | 8 | 9 |
| $C_2$ | 53 | 52 | 50 | 51 | 49 | 46 | 46 | 45 | 43 | 44 | 45 | 44 |
| $C_3$ | 36 | 35 | 34 | 33 | 37 | 41 | 41 | 43 | 44 | 38 | 40 | 41 |
| $C_4$ | 3 | 4 | 5 | 3 | 5 | 5 | 5 | 5 | 5 | 6 | 7 | 7 |
| $C_{5+}$ | 0 | 0 | 0 | 0 | 0 | 0 | 0 | 0 | 0 | 0 | 0 | 0 |
| Ar | 0 | 0 | 0 | 0 | 0 | 0 | 0 | 0 | 0 | 0 | 0 | 0 |
| $CO_2$ Yield, % (2) | 24 | 20 | 18 | 16 | 32 | 31 | 30 | 29 | 29 | 32 | 32 | 32 |
| CO Conv., % (2) | 50 | 41 | 38 | 33 | 71 | 67 | 66 | 64 | 64 | 81 | 76 | 75 |

(1) 400° C., 735 psig (5169 kPa), Actual Hourly Space Velocity = 50.
(2) Based on carbon.
(3) Weight ratio: Cr—Zn/Pt-AW500 = 1.3

The data show that as the molar ratio of $H_2$ to CO increased, the $C_{2+3}$ yield of the composotion increased. Compare the $C_{2+3}$ yield at a ratio of 0.5 versus the $C_{2+3}$ rield at a ratio of 2.0.

EXAMPLE 10

The example compares the catalytic properties of a prior art composition with a composition of the present invention for the conversion of synthesis gas. All of the compositions were prepared in accordance with Example 2, except the prior art type was prepared in the hydrogen form. All runs were conducted at 735 psig (5169 kPa) in a 310 stainless steel tubular reactor at an actual hourly space velocity of 50.

TABLE X

SYNGAS REACTIONS
Cr—Zn PHYSICAL MIXTURES WITH
$H^+$ OR Pd-ZSM-5 (1)

| Catalyst (2) | HZSM-5 (Prior Art Type) | | | | | | Pd-ZSM-5 | | | |
|---|---|---|---|---|---|---|---|---|---|---|
| Time, hrs. | 3 | 22 | 26 | 45 | 50 | 68 | 3 | 22 | 26 | 45 |
| $C_{2+3}$ Yield, % (3) | 15 | 12 | 12 | 11 | 11 | 11 | 27 | 25 | 24 | 24 |
| $C_{2+3}$ Sel., % (3) | 53 | 46 | 45 | 37 | 38 | 38 | 85 | 77 | 78 | 79 |
| HC Yield, % (3) | 28 | 26 | 26 | 30 | 29 | 28 | 32 | 32 | 31 | 31 |
| HC Sel., % (3) | | | | | | | | | | |
| $C_1$ | 7 | 7 | 8 | 6 | 6 | 7 | 9 | 7 | 7 | 8 |
| $C_2$ | 14 | 11 | 12 | 10 | 10 | 10 | 44 | 33 | 33 | 32 |
| $C_3$ | 39 | 35 | 33 | 27 | 28 | 28 | 41 | 44 | 45 | 47 |
| $C_4$ | 13 | 18 | 16 | 20 | 21 | 21 | 5 | 9 | 9 | 9 |
| $C_{5+}$ | 4 | 8 | 10 | 20 | 21 | 21 | 0 | 3 | 3 | 2 |
| Ar | 22 | 20 | 21 | 17 | 14 | 13 | 0 | 3 | 3 | 3 |
| $CO_2$ Yield, & (3) | 29 | 29 | 29 | 27 | 27 | 27 | 29 | 28 | 28 | 28 |

(1) 400° C., $H_2/CO$ = 1, 735 psig, Actual Hourly Space Velocity = 50.
(2) Molar Ratio: Cr:Zn:Al:Pd:ZSM-5(Al).
HZSM-5 20:51:0.3:0:1.
Pd-ZSM-5 20:51:0.3:0.5:1.
(3) Based on Carbon.

These data show that palladium-exchange of ZSM-5 in accordance with the present invention gave a much higher $C_{2+3}$ selectivity and yield than prior art ($H^{30}$-ZSM-5) compositions.

Obviously, other modifications and variations of the present invention are possible in the light of the above teachings. It is, therefore, to be understood that changes may be made in the particular embodiments of this invention which are within the full intended scope of the invention as defined by the appended claims.

What is claimed is:

1. A method for the conversion of synthesis gas comprising:
   contacting synthesis gas which comprises hydrogen and carbon monoxide with a catalytically effective amount of a crystalline aluminosilicate composition, under conversion conditions effective to provide $C_{2+3}$ hydrocarbons at a carbon yield of at least about 20% and a carbon selectivity of at least about 80%, said conversion conditions comprising a temperature of 325°–500° C. and a pressure of 50–1000 psig and said aluminosilicate composition being prepared by a method which comprises:

(a) contacting a crystalline aluminosilicate with a platinum or palladium salt solution to provide a platinum or palladium crystalline aluminosilicate containing about 0.2 to about 5.0% by weight of platinum or palladium, said crystalline aluminosilicate being ZSM-5 or chabazite;

(b) calcining the platinum or palladium crystalline aluminosilicate in air at a temperature of about 300° C. to about 600° C. for at least 4 hours;

(c) heating the calcined palladium or platinum crystalline aluminosilicate in the presence of hydrogen from ambient temperature to an elevated temperature of about 300° C. to about 400° C. at a rate of temperature increase of about 0.5 to about 2.0° C. per minute;

(d) maintaining said crystalline aluminosilicate at said elevated temperature for about 0.75 to about 1.25 hours;

(e) cooling said crystalline aluminosilicate to ambient temperature in the presence of hydrogen; and (f) mixing said crystalline aluminosilicate with a methanol synthesis catalyst in a weight ratio of methanol synthesis catalyst to crystalline aluminosilicate of about 0.3 to about 5, said methanol synthesis catalyst comprising chromium oxide-zinc oxide or copper oxide-zinc oxide.

2. A method according to claim 1, where in step (a) said platinum or palladium salt solution is ion-exchanged onto said crystalline aluminosilicate.

3. A method according to claim 1, where in step (a) said platinum or palladium salt solution is impregnated onto said crystalline aluminosilicate.

* * * * *